(12) United States Patent
Horger et al.

(10) Patent No.: US 7,292,720 B2
(45) Date of Patent: Nov. 6, 2007

(54) METHOD AND MAGNETIC RESONANCE TOMOGRAPHY APPARATUS FOR GRAPHIC PLANNING OF ANGIOGRAPHIC EXPOSURES USING A CONTRAST AGENT

(75) Inventors: Wilhelm Horger, Schwaig (DE); Gerhard Laub, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 847 days.

(21) Appl. No.: 10/614,444

(22) Filed: Jul. 7, 2003

(65) Prior Publication Data
US 2004/0008028 A1 Jan. 15, 2004

(30) Foreign Application Priority Data
Jul. 9, 2002 (DE) .............................. 102 30 877

(51) Int. Cl.
*G06K 9/00* (2006.01)
(52) U.S. Cl. ...................................... 382/131; 600/420

(58) Field of Classification Search ................ 382/128, 382/130, 131; 600/410, 420, 431; 715/808, 715/961, 965
See application file for complete search history.

(56) References Cited

U.S. PATENT DOCUMENTS 6,662,038 B2* 12/2003 Prince ........................ 600/420
2006/0183996 A1* 8/2006 Abe et al. .................... 600/410

* cited by examiner

*Primary Examiner*—Andrew W. Johns
(74) *Attorney, Agent, or Firm*—Schiff Hardin LLP

(57) ABSTRACT

In a method and processing device for a magnetic resonance tomography apparatus, with which a test bolus measurement is conducted for a subsequent angiography measurement using contrast agent, a test bolus pop-up is displayed in an interactive graphic user interface, and a time curve of at least the arterial contrast agent concentration is automatically determined from the test bolus measurement and presented in the test bolus pop-up, for time planning of the subsequent angiography measurement.

19 Claims, 5 Drawing Sheets

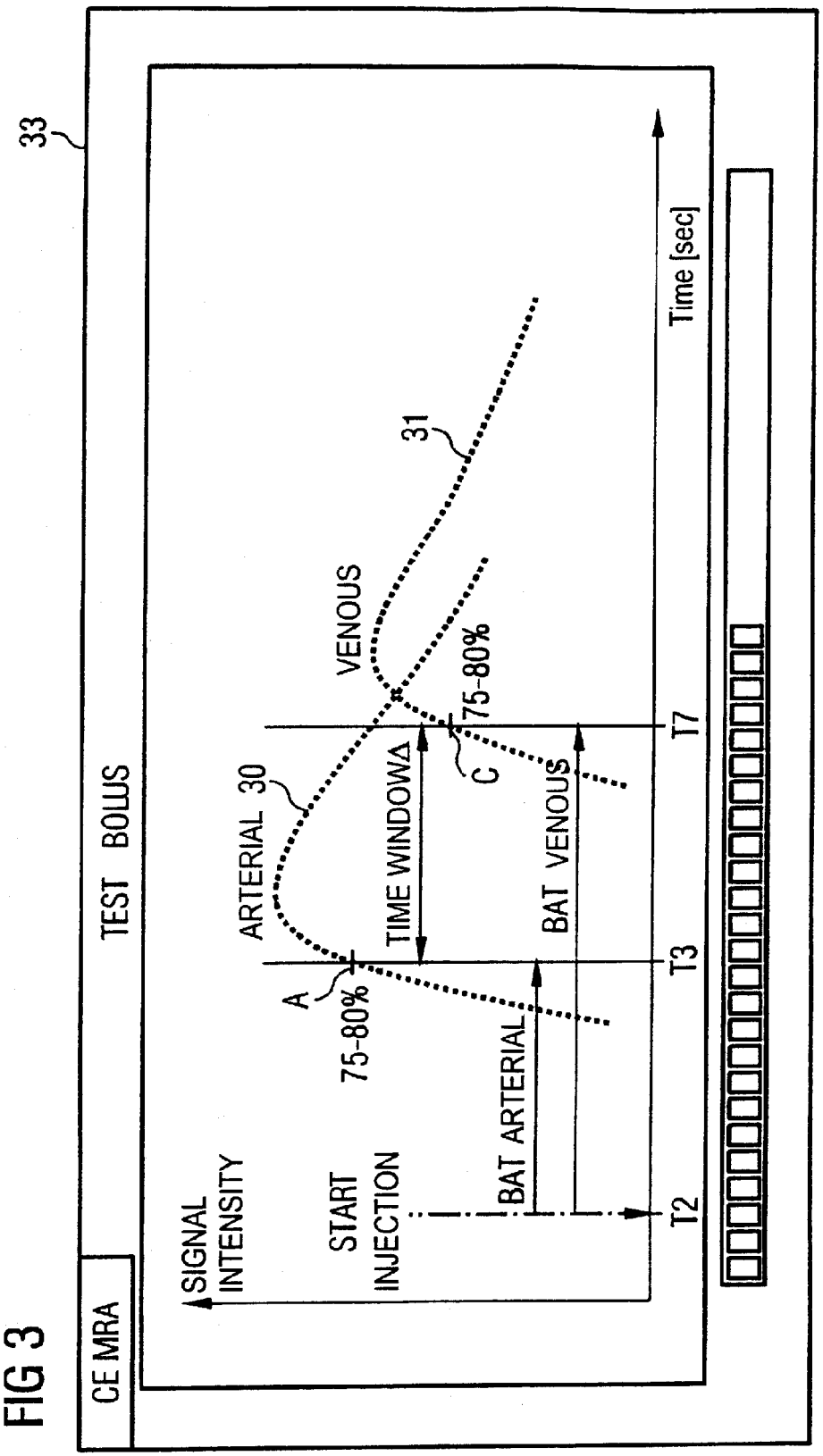

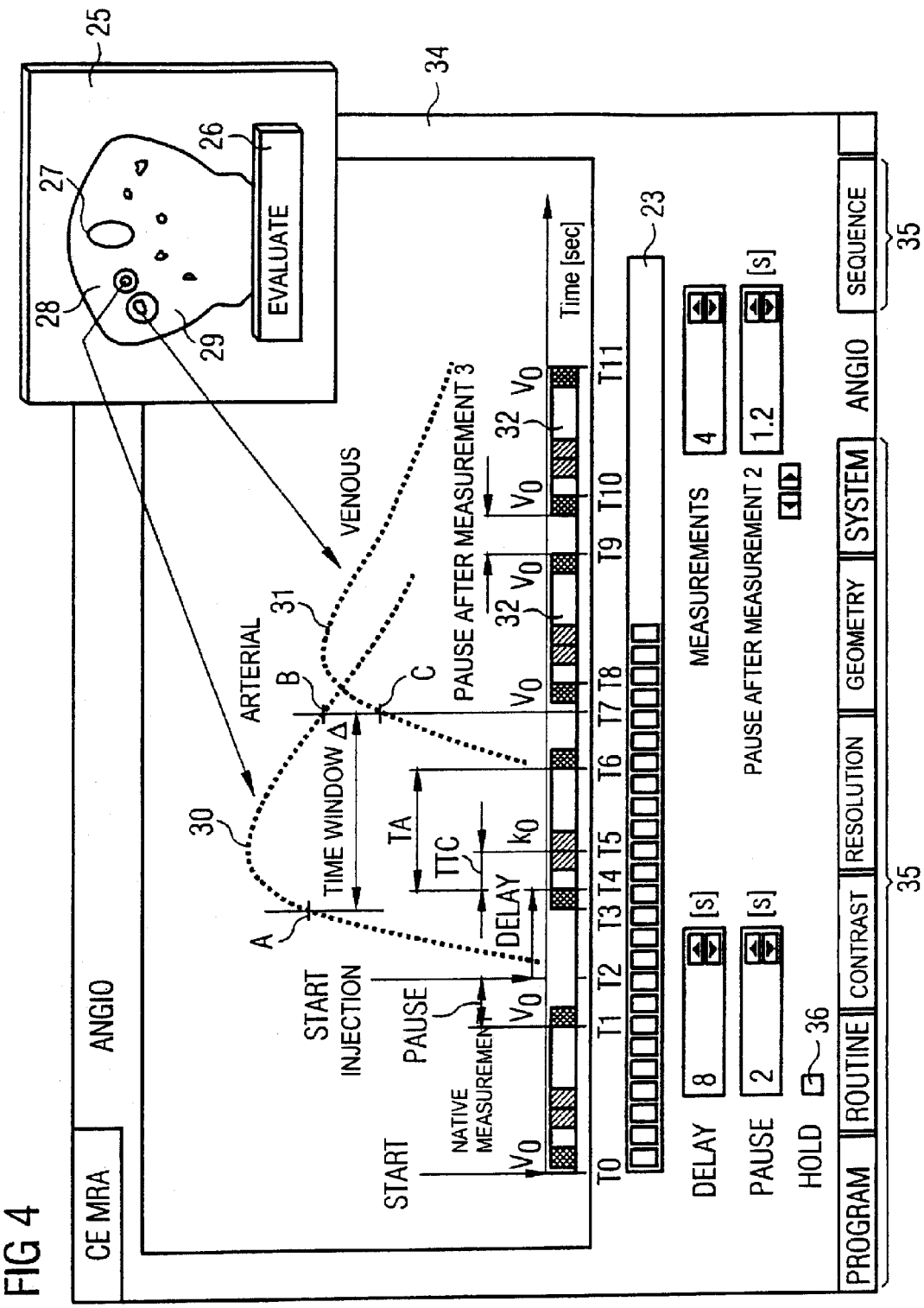

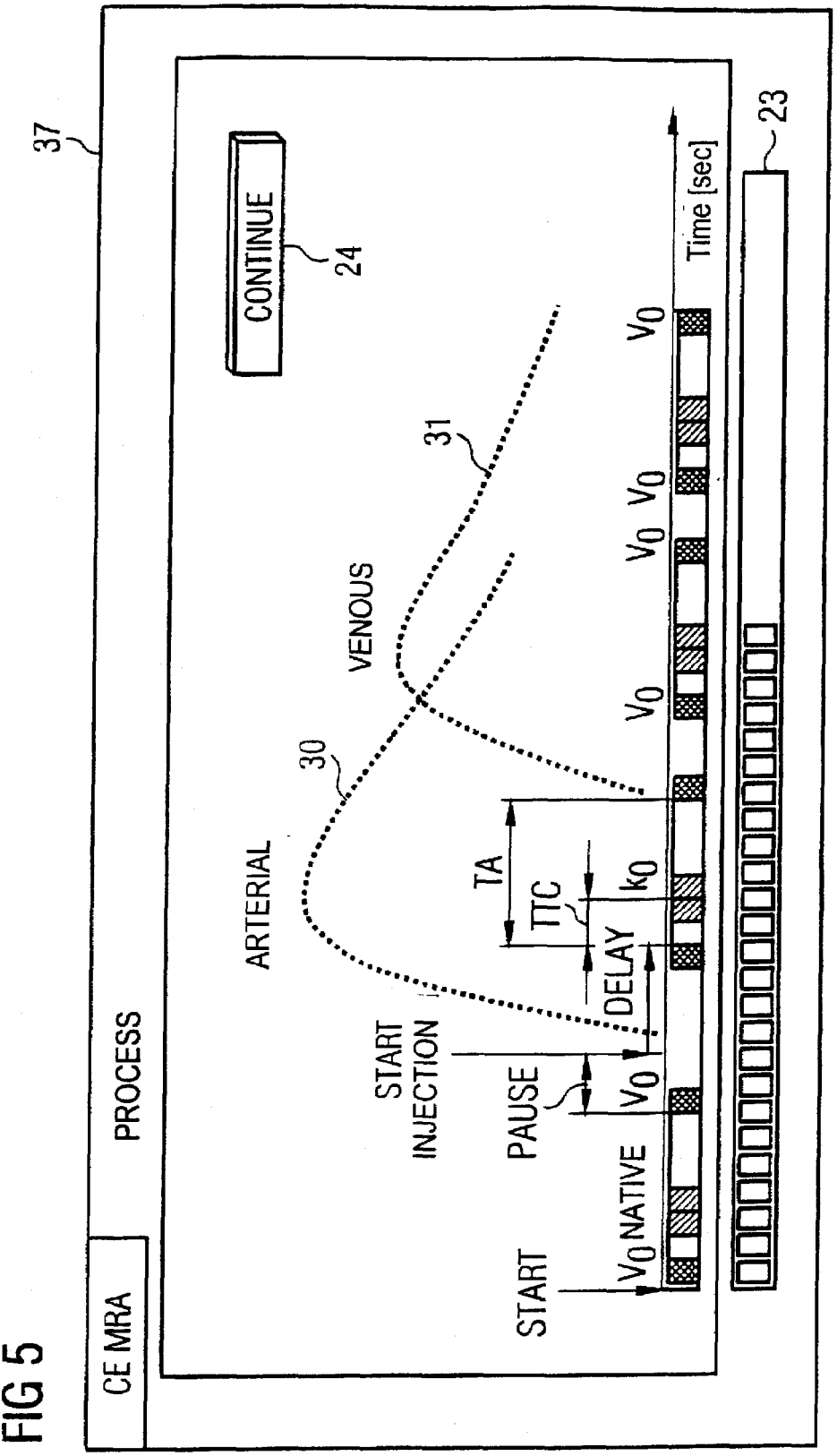

METHOD AND MAGNETIC RESONANCE TOMOGRAPHY APPARATUS FOR GRAPHIC PLANNING OF ANGIOGRAPHIC EXPOSURES USING A CONTRAST AGENT

BACKGROUND OF THE INVENTION

1. Field of the Invention

The present invention is directed in general to nuclear magnetic resonance tomography (MRT) as employed in medicine for examining patients. The present invention is more specifically directed to a magnetic resonance tomography apparatus with a device for graphic planning of angiographic MRT measurements that are made using a contrast agent.

2. Description of the Prior Art

MRT is based on the physical phenomenon of nuclear magnetic resonance and has been utilized for more than 15 years as an imaging method in medicine and biophysics. In this examination method, the subject is exposed to a strong, constant magnetic field. As a result, the nuclear spins of the atoms in the subject align, these having been previously irregularly oriented. Radiofrequency energy can then excite these "ordered" spins to a specific resonance. This resonance generates the actual measured signal in MRT that is picked up by suitable reception coils. The signals from examination subject can be spatially encoded in all three spatial directions by employing non-uniform magnetic fields generated by gradient coils, generally referred to as "location encoding".

The acquisition of the data in MRT ensues in k-space (frequency domain). The MRT data in the image domain are operated on means of a Fourier transformation to produce the k-space data. The location encoding of the subject that k-space erects ensues by means of gradients in all three spatial directions. A distinction is made between the slice selection gradient (determines an exposure slice in the subject, usually along the z-axis), the frequency encoding gradient (determines a direction in the slice, usually the x-axis) and the phase encoding gradient (determines the second dimension within the slice, usually the y-axis). The selected slice can be subdivided into further slices by phase encoding along the z-axis.

Thus, a slice first is selectively excited, for example in the z-direction, and a phase encoding can be implemented in z-direction. The encoding of the location information in the slice ensues by a combined phase encoding and frequency encoding by means of these two, aforementioned orthogonal gradient fields, which, for the example of a slice excited in the z-direction, are generated in the x-direction and the y-direction by the aforementioned gradient coils.

In order to measure an entire slice of the examination subject, the imaging sequence (for example, gradient echo sequence such as the FLASH sequence) is repeated N times for different values of the phase encoding gradient, for example $G^y$. The time spacing of the respective RF excitation pulses is referred to as the repetition time TR. At every sequence execution, the magnetic resonance signal (for example, the gradient echo signal) is likewise sampled, digitized and stored by a $\Delta t$-clocked ADC (analog-to-digital converter) N times in equidistant time steps $\Delta t$ in the presence of the readout gradient $G^x$. In this way, a number matrix that is produced row by row (k-space matrix or k-matrix) is obtained with N×N data points. An MR image of the slice under observation can be directly reconstructed with a resolution of N×N pixels from this dataset by means of Fourier transformation (a symmetrical matrix with N×N points is only an example; asymmetrical matrices also can be generated). For physical reasons, the data entries (values) in the region of the center of the k-matrix mainly contain information about the contrast and the entries in the edge region of the k-matrix mainly contain information with respect to the resolution of the transformed MRT image.

Tomograms of the human body can be acquired in all directions in this manner. MRT as a tomographic method in medical diagnostics is distinguished as a "non-invasive" examination method. Particularly in the case of angiographic exposures (i.e. exposures of the blood vessels in the human body, specifically in organs with blood circulation), limits exist as to the contrast that can be obtained by non-augmented MR imaging. These limits, however, can be considerably expanded by utilizing contrast agents. The functioning of contrast agents in magnetic resonance tomography is generally based on an influencing of the parameters that determine the contrast such as, for example, the longitudinal relaxation time $T_1$ or the transverse relation time $T_2$. Tri-valent gadolinium $Gd^{3+}$, which has a $T_1$-shortening effect, has prevailed in clinical applications. Gadolinium losses its toxicity by being bonded in chelate complexes (DTPA, diethylene triamine pentaacetic acid), so that Gd-DTPA usually can be intravenously applied. A vein is selected that that leads directly to the heart and that ultimately distributes the contrast agent in the entire arterial system. In standard sequences ($T_1$-weighted spin echo sequence, gradient echo sequence, etc.), the accelerated $T_1$ relaxation causes a boost of the MR signal, i.e. a brighter presentation of the appertaining tissue in the MR image. Sharp and high-contrast images of vessels in, for example, the head, neck, heart or kidneys can be obtained in this way.

Such a contrast agent-supported method in magnetic resonance tomography is generally referred to as "contrast enhanced MR angiography" (also contrast enhanced MR angiography, CE MRA). The quality of contrast agent-supported vascular exposures is significantly dependent on the time coordination of the sequence steps characterizing the measurement (data acquisition), which is generally referred to as timing or contrast agent timing. The most critical sequence steps are: contrast agent injection, measurement duration as well as measurement of the middle of the k-space matrix. The goal for achieving an optimally good contrast is to cause a maximum contrast agent concentration to be present in the region of interest to be acquired during the measurement of the middle region of the k-matrix. For this reason, contrast enhanced angiography is implemented conventionally in the following way:

1. First, overview exposures ("localizers") of a wide greatest variety of slices are acquired in order to roughly determine the position of the vascular system of interest and to derive optimum exposure slices therefrom.

2. Injection of a test bolus is implemented wherein the time curve of the contrast agent enrichment in the region of interest (ROI) is determined. To that end, a very small dose (approximately 2 ml) of contrast agent is intravenously injected at time T2 (FIG. 2), and the MR intensity of an artery situated in the ROI is subsequently measured (per second as a rule). Using evaluation software, the intensity behavior of the contrast agent 30 in the ROI can be presented, as shown in FIG. 2. The time from the beginning of the contrast agent injection T2 to the time T3 at which the contrast agent has concentrated in an adequate amount (A, B—usually 75-80% of the maximum value) is generally referred to as the transit time or bolus arrival time, BAT. On the basis of the BAT, the user subsequently calculates the delay T4 after which the actual measurement protocol (for example, the spin echo or gradient echo sequence) should be started—referenced to the point in time of the injection T2 or $T_{inj}$. For calculating the delay time (FIG. 2), the user conventionally uses a region-dependent empirical value or a trusted equation. Possible equations employed are:

Delay=$BAT-TA/4$

Delay=$BAT+T_{inj}/2-TA/2$

Delay=$BAT-TTC+15\%TA$ etc.

wherein TA designates the overall measurement time (T4 through T60 of the sequence employed and TTC (time to center) references the time following the sequence start T5 at which the center row of the k-matrix is measured. As shown in FIG. 2, the delay (T2 through T4) should be ideally selected or calculated such that TA occurs in the maximum region of the concentration (time between A and B) and additionally so the center row of the k-matrix is measured after the time TTC (T5) with maximum contrast agent concentration in the ROI. The test bolus measurement thus serves for preparing for the actual measurement, i.e. the time planning in order to be able to optimize the contrast of the actual CE MRA measurement.

3. After the test bolus measurement, a pre-contrast measurement is implemented, i.e. an MR measurement without a contrast agent. In such a basic exposure without a contrast agent injection, signals are acquired from tissue in the ROI that is of no interest, but which will likewise be seen in the following contrast agent exposure (post-contrast measurement). This tissue is calculated out in the last step of the CE MRA method by means of a subsequent subtraction of the pre-contrast and post-contrast measurements.

4. The administration of the contrast agent in an increased dose (approximately 20 ml) then ensues manually at the end of the pre-contrast measurement.

5. The post-contrast measurement, i.e. the start and the execution of the selected or set MR sequence, ensues after the calculated or set delay time.

6. In the last step of the CE MRA, the exposures (scan results) of the pre-contrast and post-contrast measurements are subtracted at the image level in the form of a post-processing.

A CE MRA measurement as described above and conventionally implemented is characterized by an extremely deterministic executive sequence. The time planning of the measurement procedure is based essentially on rigid formulas without taking further physiological factors into consideration. This can result in the measurement not ensuing at the optimum point in time. If the measurement is started too early, then the center region of the k-matrix contains the contrast information measured at a point in time at which the contrast agent concentration in the ROI is not yet optimum. The consequence thereof is a poor image quality due to the appearance of artifacts in the form of edge oscillations (Gibbs ringing) that make the measurement unusable. If the measurement is started too late, the enrichment of contrast agent that is already occurring in the venous part of the vascular system leads to a superimposition of veins and arteries in the exposure and the exposure thus is likewise unusable.

SUMMARY OF THE INVENTION

It is an object of the present invention to facilitate or optimize the time planning of a contrast agent-supported angiographic MRT measurement for the user of an MRT apparatus.

This object is inventively achieved by the use of a processing device in a magnetic resonance tomography apparatus having a display for the graphic presentation of interactive user interfaces via which the magnetic resonance tomography apparatus can be configured by entering and/or selecting parameters. The result of a preparatory test bolus measurement wherein the time curve of the arterial contrast agent concentration is determined for the time planning of a contrast agent-supported magnetic resonance angiography measurement is graphically displayed in the form of a test bolus pop-up on a graphically displayed user interface.

Differing from the conventional techniques, the time curve of the venous contrast agent concentration is also taken into consideration and graphically presented in the test bolus pop-up according to the present invention.

The evaluation of a test bolus measurement is simplified in accordance with the invention by the processing device calculating a standard deviation image from the acquired image series of a test bolus measurement, this standard deviation image being displayed and the arterial and venous regions to be evaluated being marked therein and evaluated with respect to the entire series.

In order to be able to match the time behavior of the enrichment with contrast agent to the point in time of the measurements, the MR measurement protocols are, in accordance with the invention, graphically displayed true-to-scale in the form of measurement bars, in addition to the curves of the venous and arterial contrast agent concentration.

A graphic planning of the CE MRA measurement ensues in accordance with the invention by the measurement bars being displaced relative to one another as well as relative to the curves of the venous and arterial contrast agent concentration.

The displacement thereby inventively ensues in a simple way a mouse or by entering values into corresponding input windows.

According to the present invention, the course of the measurement can be tracked on the basis of a time-lapse bar.

Advantageously, a further PROCESS pop-up is generated for observing the course of the measurement on the basis of a time-lapse bar.

The above object also is achieved in accordance with the invention in a method for the graphic planning of a contrast agent-supported angiographic MRT measurement in a magnetic resonance tomography apparatus, which proceeds as described above.

The above object also is achieved in accordance with the invention in a computer software product that implements the aforementioned method when it runs on a computer device connected to a magnetic resonance tomography apparatus.

DESCRIPTION OF THE DRAWINGS

FIG. 3 illustrates an inventive test bolus pop-up for determining the optimum measurement region of a contrast agent-supported angiographic MR measurement, taking the time-delayed contrast agent concentration in the venous system into consideration.

FIG. 4 illustrates an expanded pop-up in the form of an inventive ANGIO pop-up wherein, first, the evaluation of the test bolus measurement is optimized and, second, a contrast agent-supported angiographic MR measurement can be graphically planned.

FIG. 5 illustrates an inventive PROCESS pop-up wherein a graphically planned contrast agent-supported angiographic MR measurement can be tracked in terms of its temporal course.

DESCRIPTION OF THE PREFERRED EMBODIMENTS

Figure 1:
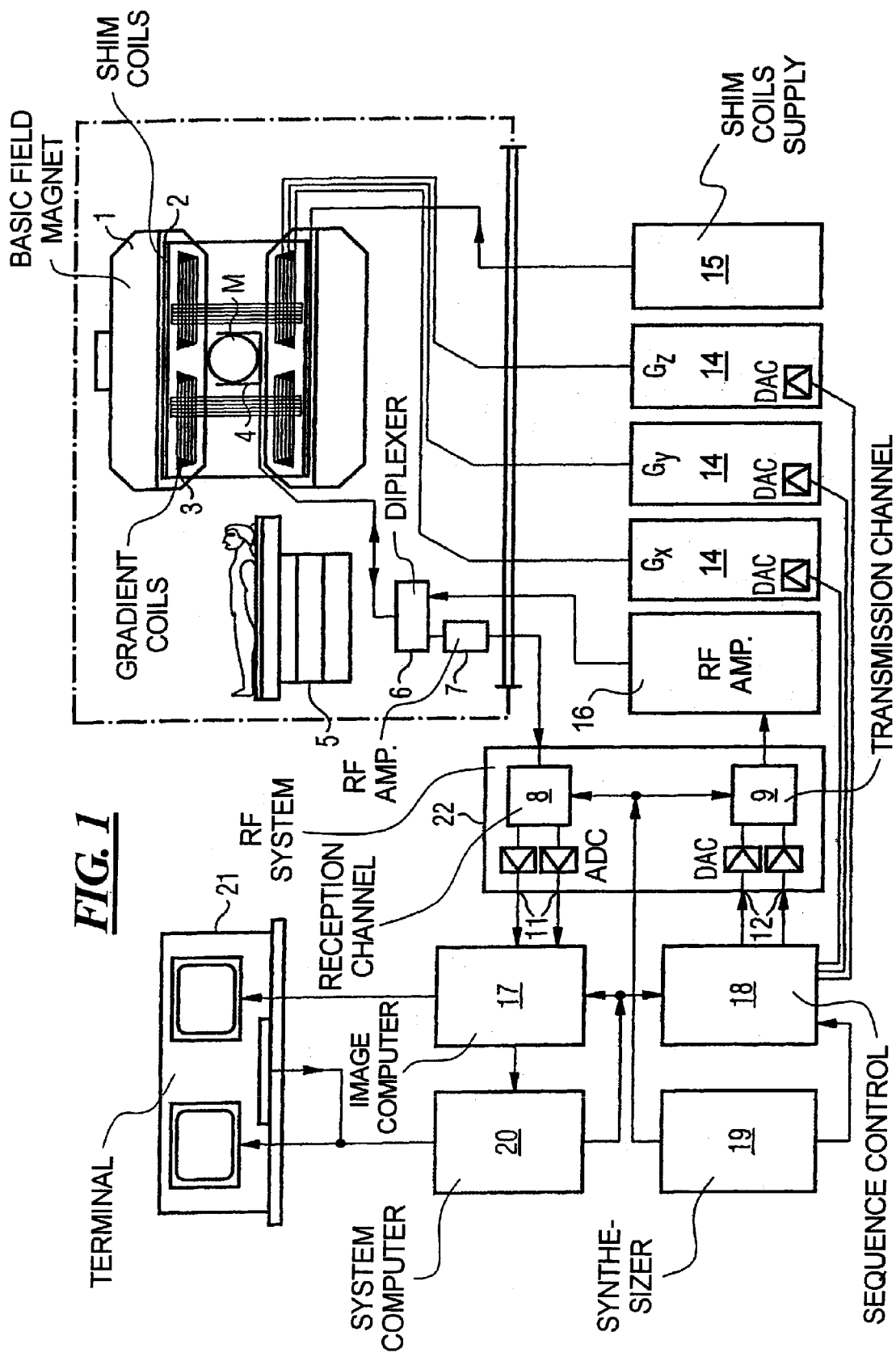
FIG. 1 schematically illustrates a magnetic resonance tomography apparatus operable in accordance with the invention.

FIG. 1 is a schematic illustration of a magnetic resonance tomography apparatus with improved contrast behavior for MR time-of-flight angiography exposures according to the present invention. The basic components of the magnetic resonance tomography apparatus corresponds to those of a conventional tomography apparatus, with the differences described below. A basic field magnet 1 generates a temporally constant, strong magnetic field for the polarization or alignment of the nuclear spins in the examination region of a subject such as, for example, a part of a human body to be examined. The high homogeneity of the basic magnetic field required for a magnetic resonance measurement is defined in a spherical measuring volume M into which the parts of the human body to be examined are introduced. Shim plates of ferromagnetic material are attached at a suitable location for achieving the homogeneity requirements and, in particular, for eliminating time-invariable influences. Time-variable influences are eliminated by shim coils 2 that are driven by a shim power supply 15.

A cylindrical gradient coil system 3 that is composed of three windings is introduced into the basic field magnet 1. Respective amplifiers 14 supply the windings with current for generating a linear gradient field in the respective directions of the Cartesian coordinate system. One winding of the gradient field system 3 generates a gradient $G_x$ in the x-direction, another generates a gradient $G_y$ in the y-direction, and another generates a gradient $G_z$ in the z-direction. Each amplifier 14 has a digital-to-analog converter that is driven by a sequence controller 18 for generating the gradient pulses at the correct times.

A radiofrequency antenna 4 is situated within the gradient field system 3. The radiofrequency antenna 4 converts the radiofrequency pulses from a radiofrequency power amplifier 30 into a magnetic alternating field for exciting the nuclei and alignment of the nuclear spins of the examination subject or of the region of the subject to be examined. The sequence controller 189 also controls the power amplifier 30, in a sequence COM posed of one or more radiofrequency pulse and one or more gradient pulses. The radiofrequency antenna 4 also converts the alternating field produced by the precessing nuclear spins, i.e. the magnetic resonance echo signals, into a voltage that is supplied via an amplifier 7 to a radiofrequency reception channel 8 of a radiofrequency system 22. The radiofrequency system 22 also has a transmission channel 9 in which the radiofrequency pulses for the excitation of magnetic resonance are generated. The respective radiofrequency pulses are digitally represented as a sequence of complex numbers in the sequence controller 18 on the basis of a pulse sequence prescribed by the system computer 20. As a real part and an imaginary part, this number sequence is supplied via respective inputs 12 to a digital-to-analog converter in the radiofrequency system 22 and from there to the transmission channel 9. In the transmission channel 9, the pulse sequences are modulated onto a radiofrequency carrier signal having a base frequency corresponding to the resonant frequency of the nuclear spins in the measuring volume.

Switching from transmission mode to reception mode ensues via a transmission-reception duplexer 6. The radiofrequency antenna 4 emits the radiofrequency pulses for exciting the nuclear spins into the measuring volume M and samples resulting echo signals. The correspondingly acquired magnetic resonance signals are phase-sensitively demodulated in the reception channel 8 of the radiofrequency system 22 and are converted into a real part and an imaginary part of the measured signal via respective analog-to-digital converters. An image computer 17 reconstructs an image from the measured data acquired in this way. The administration of the measured data, image data and control programs ensues via the system computer 20. On the basis of a prescription with control programs, the sequence controller 18 controls the generation of the desired pulse sequences and the corresponding sampling of k-space. In particular, the sequence controller 18 controls the switching of the gradients at the correct times, the emission of the radiofrequency pulses with defined phase and amplitude as well as the reception of the magnetic resonance signals. The time base for the radiofrequency system 22 and the sequence controller 18 is made available by a synthesizer 19. The configuration of the MRT apparatus, the selection of corresponding control programs for generating a nuclear magnetic resonance image as well as the presentation of the generated nuclear magnetic resonance image ensue via a terminal 21 that has a keyboard as well as one or more picture screens.

Different pop-ups can be called on the picture screen of the terminal 21 for the configuration of the MRT apparatus. Input windows are displayed in these pop-ups and the user can input measurement parameter values therein and, thus, undertake MRT device settings. For example, there is thus a CONTRAST pop-up in which—among other things—the flip angle can be set, a ROUTINE pop-up in which, for example, the echo time, the repetition time, the number of slices can be input, a RESOLUTION pop-up in which the k-matrix can be configured, a SEQUENCE pop-up in which the desired sequence type (gradient echo sequence, steady-state spin echo sequence, true-Fisp, EPI, FLASH, etc.) can be selected, etc.

Figure 2:
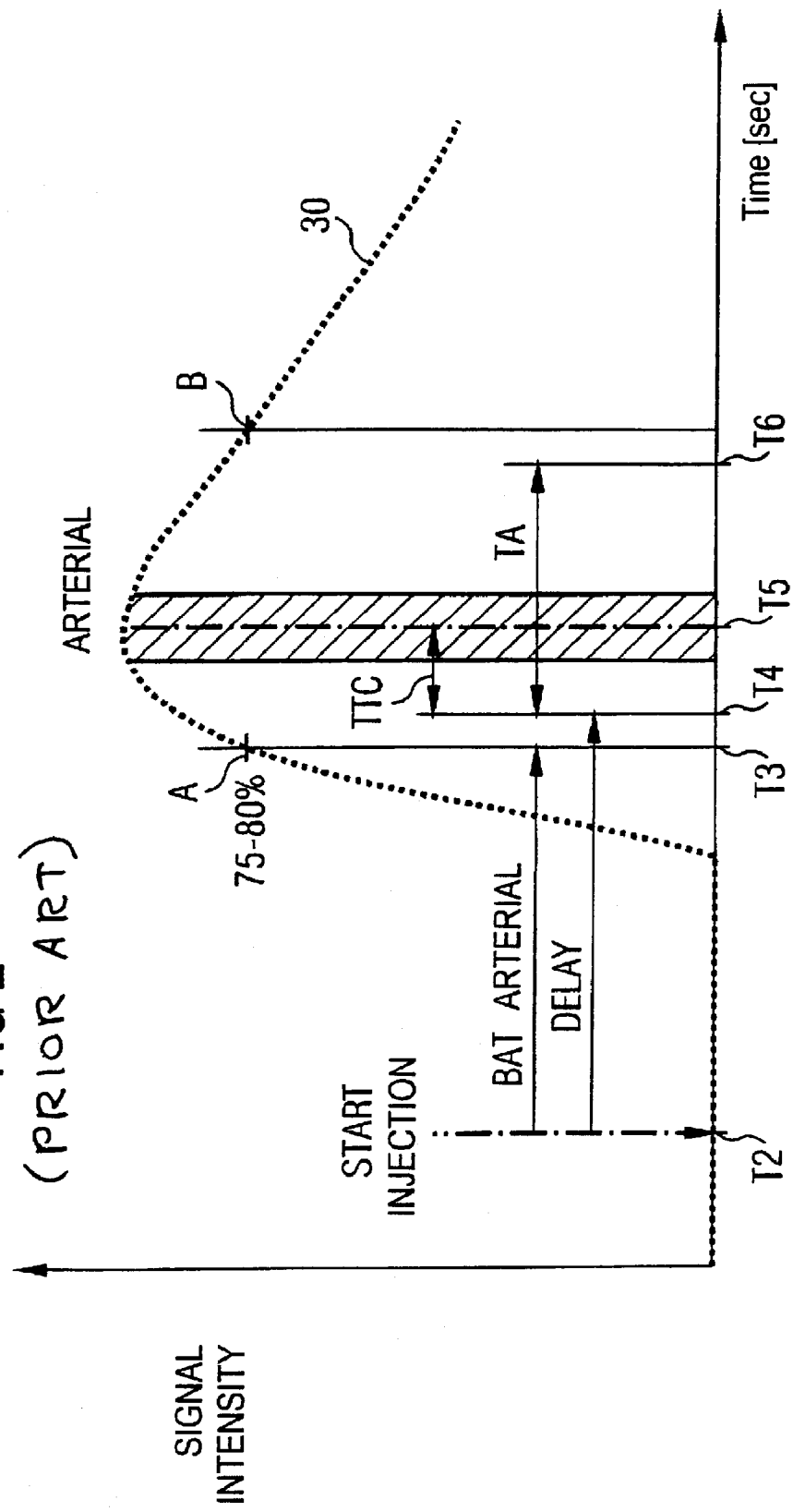
FIG. 2 is a diagram of a conventional test bolus measurement for determining the behavior of the arterial contrast agent concentration in the region of interest.

One purpose of the present invention is to also offer the user a pop-up for the test bolus measurement. Such a TEST BOLUS pop-up 33 is shown in FIG. 3. First, the curve 30 of the contrast agent concentration after the point in time of the injection T2 is graphically presented in this TEST BOLUS popup 33 as the result of an evaluated test bolus measurement—the user implements the evaluation by means of evaluation software. Further, the transit time T3 (BAT arterial) is automatically determined from the graphic in the invention. A further purpose of the present invention is to present the curve 31 of the contrast agent concentration in the veins in this TEST BOLUS pop-up 33 and to automatically determine the venous transit time T7 (BAT venous). In contrast to the conventional test bolus measurement (FIG. 2), thus, two curves 30, 31 of the contrast agent concentration are inventively presented in this TEST BOLUS pop-up 33 in that the arterial contrast agent concentration is augmented by the contrast agent concentration in the veins.

The influence that the venous contrast agent concentration can have on a CE MRA measurement has already been mentioned: When the post-contrast measurement (TA) is temporally located in the region of a significant contrast agent concentration in the venous system (Delay+TA>BAT venous), then arterial and venous vessels superimpose on the image; the exposure is unusable. According to the present invention, the venous contrast agent concentration 31 therefore generally should be taken into consideration in the measurement planning given CE MRA exposures. To that end, the automatic evaluation in the TEST BOLUS pop-up 33 supplies two transit times T3, T7 (BAT arterial and BAT venous) the time difference therebetween being referred to as a time window Δ (T3 through T7, region between A and C). When the measurement time TA of the post-contrast measurement is less than this time window (TA<Δ), then the post-contrast measurement usually will be started in the time Delay=BAT arterial after the injection (T3=T4 thus applies). When the measurement time of the post-contrast measurement is greater than this time window (TA>Δ), then the beginning of the post-contrast measurement is calculated according to the following equation:

Delay=BAT arterial=TTC+Δ/2.

In general, the time curve of the contrast agent concentration in the arterial system 30 as well as in the venous system 31, and thus the time window Δ as well, is dependent on the respective blood circulation situation. This is patient-dependent (low blood pressure) as well as pathology-dependent (poor circulation of the vessels due to inflammations, deposits, constrictions) as well as region-dependent (intracranial regions (skull), for example, exhibit a Δ of approximately 5 seconds, neck and lung vessels 4 through 8 seconds, kidneys and abdominal arteries up to 10 seconds, vessels in the pelvis 20 through 30 seconds, peripheral vessels up to 60 seconds, etc.). As a result of the experimental determination of both curves 30, 31 in the initial stage of a CE MRA measurement, thus, the measurement planning can be inventively individually adapted to the currently existing situation.

FIG. 4 shows an expanded TEST BOLUS pop-up 33 in the form of an inventive ANGIO pop-up 34 in which, first, the evaluation of the test bolus measurement is inventively optimized and, second, a contrast agent-supported angiographic MR measurement can be inventively graphically planned.

As already mentioned, a test bolus measurement (arterial or venous) is designed such that a series of images of a slice (usually 1 image per second) is acquired at T2 following the injection of a small contrast agent dose. The conventional evaluation of this test bolus measurement according to the Prior Art ensues in such a way that the user must start evaluation software that makes it possible to view each image individually. The user must locate the region of an artery or vein by comparing the individual images (on the basis of changes in intensity), and must mark this region and initiate the evaluation software to graphically present the intensity curve 30, 31 of the marked region according to FIG. 2 or FIG. 3.

In the present invention, the evaluation of the test bolus measurement(s) is automated, and thus simplified. After an image series of a slice has been acquired in the framework of a test bolus measurement, the user is inventively presented with a standard deviation (STD DEV) image 25 of this image series in the ANGIO pop-up 34. Such a STD DEV image 25 is shown at the upper right in FIG. 4. For example, it is generated by the system computer 20 in that this computer 20 adds the intensities of the individual images of the series. The STD DEV image 25 in FIG. 4 represents a section through the neck; the trachea 27 can be seen therein as a black region, veins 29 and arteries 28 as bright points. On the basis of his/her anatomical expertise, the user must now mark arteries 28 and veins 29 with circles. Arterial and venous curves 30, 31 of the contrast agent concentration are graphically presented in the ANGIO pop-up 34 by activating the EVALUATE button 26.

The inventive simplification means that the user no longer has to open evaluation software (evaluation tool) in order to select images therein. Immediately after the end of the test bolus measurement, the interface of the ANGIO pop-up 34 offers an overview image 25 in which the user can immediately recognize the relevant regions 28, 29 to be marked. The marking of the vessels can be also automated with suitable algorithms.

Another feature of the present invention is implemented in the ANGIO pop-up 34 of FIG. 4: The user is presented with the possibility in the ANGIO pop-up 34 of graphically planning a contrast agent-supported angiographic MR measurement. To that end, individual measurements in the form of measuring bars 32 are displayed under the time axis and these can be coordinated as to time with the contrast curves 30, 31. The situation in FIG. 4 shows four measuring bars 32 that respectively comprise different time intervals from one another. The number of measurements can be defined with the input field "MEASUREMENTS". As in the prior art, the first measurement—as pre-contrast measurement—always represents a basic measurement (without contrast agent) of the slice of interest. The following post-contrast measurements record the same slice under the influence of the contrast agent.

The breathing instructions (voice output, VO) shown black in FIG. 4 that are provided immediately before and immediately after each measurement via pre-configured sound datafiles assure that each measurement is implemented with the same body posture and assure that the anatomical situation of the slice to be measured does not change. For example, the breathing instruction before a measurement is, "BREATH DEEPLY—HOLD YOUR BREATH". For example, the breathing instruction after a measurement is, "CONTINUE BREATHING NORMALLY".

The actual measurement involves the execution of the MR sequence that has been set and that is processed during the region (TA) marked gray. The shaded region thereby represents the time range in which the central rows of the k-matrix are sampled. This region is responsible for the contrast of the image to be acquired. The point in time in which the center of the k-matrix is exactly measured is indicated by a stroke ($k_0$) in the middle of the shaded region.

The chronological length (TA) is generally identical in all measurements but can also be selected different in order, for example, to enable different spatial resolutions in different contrast agent phases. The parameters are determined before the CE MRA experiment by selecting all sequence parameters (repetition time, echo time, sampling rate, etc.) by interaction of the user via other pop-ups, can thus not be varied in the ANGIO pop-up. Such pop-ups (PROGRAM, ROUTINE, CONTRAST, SEQUENCE, etc.) can be called by clicking the fields 35 shown in the lower region of FIG. 4 with the mouse.

An inventive graphic planning of the CE MRA measurement by means of ANGIO pop-up 34 takes place by the user arranging the individual measurements in the form of the measuring bars 32 relative to one another but mainly relative to the curves 30, 31 of the contrast agent concentration.

The time interval between the post-contrast measurements (T6-T8, T9-T10) can either be entered into the input field "PAUSE AFTER MEASUREMENT x" (x>1, x∈N) or can be displaced along the time axis with the mouse. Given a displacement with the mouse, the corresponding value is automatically updated in the input window.

The time interval between the native measurement and the first post-contrast measurement (T1 through T4) is composed of the time intervals PAUSE (T1 through T2) and DELAY (T2 through T4). Both values likewise can be varied by the user in accordance with the invention, either by manual input of the values for PAUSE and DELAY into the corresponding input window under the graphic or with the mouse. For example, the PAUSE can be modified by clicking and displacing the injection time along the time axis (this simultaneously causes a shift of the contrast agent curves). The DELAY can be varied by clicking and displacing the measuring bar of the first post-contrast measurement.

Ideally, the time intervals between the measurements, particularly the time interval between pre-contrast and post-contrast measurement (T1 through T4) should be as short as possible; the patient should be able to remain in the same position during the measurements and avoid the necessity for repositioning. Various reasons, however, require certain time intervals between the measurements, or between the measurement and the injection time. The DELAY (T2-T4), for example, should be selected such that the time of the first post-contrast measurement (TA=T4-T6) comes to lie in the time window Δ (A through C or, respectively, T3-T7) and, moreover, the measurement of the center row of the k-matrix (TTC, at T5) ensues given maximum contrast agent concentration in the arteries. In the case of extremely ill or frail patients, it may be necessary under certain circumstances to give the patient ample opportunity to breathe freely several times after holding his/her breath in order to recover strength or to recuperate. For this reason, it is possible to correspondingly set the PAUSE or to activate the HOLD button. When the HOLD button 36 is activated by a click, then the course of the CE MRA measurement stops immediately after the basic measurement (at T1). At the same time, a CONTINUE button 24 appears on the picture screen, enabling the user the continue the CE MRA measurement with the point in time of the injection T2. The PAUSE can thus be arbitrarily lengthened.

Last, the user should be provided with the possibility of graphically tracking the course of the CE MRA measurement. For this reason, a time laps bar 23 (progress bar) is implemented in the ANGIO pop-up 34 under the graphic field, for visualizing the current point in time of the CE MRA measurement. The sequence of the measurement alternatively can be presented on a separate pop-up 37 that appears on the picture screen of the terminal 21 with the start of the native measurement. Such a pop-up 37 is shown in FIG. 5 and is referred to as PROCESS pop-up 37. If the HOLD button 36 was activated in the ANGIO pop-up 34 in FIG. 4, it is meaningful to implement the CONTINUE button 24 in the PROCESS pop-up 37 in order to provide the user with the possibility of continuing the CE MRA measurement.

The features of the present invention with the corresponding advantage following therefrom are summarized below:

The graphic presentation of the result of the test bolus measurement in a separate pop-up 33 and automatic determination of the transit time (BAT) facilitates and speeds up the preparation for the time coordination of a CE MRA measurement.

Taking the time curve of the contrast agent concentration in the venous system 31 into consideration enables a better hit certainty (by defining a time window) with respect to the time coordination of the (first) post-contrast measurement.

The automatic generation of a standard deviation image 25 allows faster evaluation of the test bolus measurement.

Visualization of the pre-contrast and post-contrast measurements in the form of displaceable measuring bars 32 with simultaneous presentation of the contrast agent concentration curves 30, 31 enables a graphic and therefore more optimum and secure planning of the CE MRA measurement. As a result, the use of rigid formulas becomes superfluous.

Presentation of the temporal measurement sequence by means of a time lapse bar 23, particularly in a separate PROCESS pop-up 37, allows the user to exactly track the measurement sequence over time.

Although modifications and changes may be suggested by those skilled in the art, it is the intention of the inventors to embody within the patent warranted hereon all changes and modifications as reasonably and properly come within the scope of their contribution to the art.

We claim as our invention:

1. A processing device for a magnetic resonance tomography apparatus in which a test bolus measurement is conducted for a subsequent angiographic measurement using a contrast agent, said processing device comprising:

a processor for determining a time curve for arterial contrast agent concentration from said test bolus measurement; and a display connected to and operated by said processor for displaying an interactive graphic user interface comprising a test bolus pop-up containing said time curve of said arterial contrast agent concentration, for time planning of said subsequent angiographic measurement.

2. A processing device as claimed in claim 1 wherein said processor also determines a time curve of venous contrast agent concentration from said test bolus measurement and wherein said test bolus pop-up also contains said time curve of said venous contrast agent concentration.

3. A processing device as claimed in claim 2 wherein said test bolus measurement is comprised of a series of images, and wherein said processor calculates a standard deviation image from said series of images in said test bolus measurement, and wherein said processor operates said display to display said standard deviation image, and wherein said interactive graphic user interface allows an arterial region and a venous region in said standard deviation image to be marked in said standard deviation image and evaluated over an entirety of said series of images.

4. The processing device as claimed in claim 3 wherein said processor causes magnetic resonance measurement protocols for operating said magnetic resonance tomography apparatus to be graphically presented true-to-scale in said interactive graphic user interface represented as measuring bars correlated to said time curve of said arterial contrast agent concentration and said time curve of said venous contrast concentration.

5. A processing device as claimed in claim 4 wherein said display allows said measuring bars in said interactive graphic user interface to be displaced relative to each other and relative to the respective time curves.

6. A processing device as claimed in claim 5 further comprising a mouse connected to said processor, said mouse being manipulatable to displace said measuring bars.

7. A processing device as claimed in claim 5 wherein said display includes, in said interactive graphic user interface, an input window into which input values are enterable by a user to displace said measuring bars.

8. A processing device as claimed in claim 7 wherein said processor causes said display to include, in said interactive graphic user interface, a PROCESS pop-up presenting said time course of said test bolus measurement and including said time lapse bar.

9. A processing device as claimed in claim 4 wherein said processor causes said display to include, in said interactive graphic user interface, a time lapse bar providing a graphical indication of a time course of said test bolus measurement.

10. A method for operating a magnetic resonance tomography apparatus in which a test bolus measurement is conducted for a subsequent angiographic measurement using a contrast agent, said processing device comprising the steps of:

in a processor, determining a time curve for arterial contrast agent concentration from said test bolus measurement; and displaying an interactive graphic user interface comprising a test bolus pop-up containing said time curve of said arterial contrast agent concentration, for time planning of said subsequent angiographic measurement.

11. A method as claimed in claim 10 comprising, in said processor, also determining a time curve of venous contrast agent concentration from said test bolus measurement and also displaying said time curve of said venous contrast agent concentration in said test bolus pop-up.

12. A method as claimed in claim 11 wherein said test bolus measurement is comprised of a series of images, and comprising, in said processor, calculating a standard deviation image from said series of images in said test bolus measurement, and displaying said standard deviation image, and via said interactive graphic user interface, marking an arterial region and a venous region in said standard deviation image in said standard deviation image and for evaluating over an entirety of said series of images.

13. A method as claimed in claim 12 comprising graphically pre-seating magnetic resonance measurement protocols for operating said magnetic resonance tomography apparatus true-to-scale in said interactive graphic user interface represented as measuring bars correlated to said time curve of said arterial contrast agent concentration and said time curve of said venous contrast concentration.

14. A method as claimed in claim 13 comprising allowing said measuring bars in said interactive graphic user interface to be displaced relative to each other and relative to the respective time curves.

15. A method as claimed in claim 14 displacing said measuring bars by manipulating a mouse connected to said processor.

16. A method as claimed in claim 14 comprising displaying, in said interactive graphic user interface, an input window, and entering input values are into said input window to displace said measuring bars.

17. A method as claimed in claim 14 comprising including, in said interactive graphic user interface, a time lapse bar providing a graphical indication of a time course of said test bolus measurement.

18. A method as claimed in claim 17 comprising including, in said interactive graphic user interface, a PROCESS pop-up presenting said time course of said test bolus measurement and including said time lapse bar.

19. A computer-readable medium encoded with a data structure, said medium being loadable into a processing device, having a display connected thereto, of a magnetic resonance tomography apparatus in which a test botus measurement is conducted for a subsequent angiographic measurement using a contrast agent, and said data structure causing processing device to:

determine a time curve for arterial contrast agent concentration from said test bolus measurement; and display, on said display, an interactive graphic user interface comprising a test bolus pop-up containing said time curve of said arterial contrast agent concentration, for time planning of said subsequent angiographic measurement.

* * * * *